United States Patent [19]
Conrow

[11] Patent Number: 6,015,922
[45] Date of Patent: Jan. 18, 2000

[54] N-ALKYL-N-ALKOXYCARBOXAMIDES AND METHODS OF USE IN PROSTAGLANDIN SYNTHESIS

[75] Inventor: Raymond E. Conrow, Crowley, Tex.

[73] Assignee: Alcon Laboratories, Inc., Fort Worth, Tex.

[21] Appl. No.: 09/216,564

[22] Filed: Dec. 18, 1998

Related U.S. Application Data

[60] Provisional application No. 60/068,114, Dec. 19, 1997.

[51] Int. Cl.$^7$ .................................................. C07C 405/00
[52] U.S. Cl. ........................................... 560/312; 556/419
[58] Field of Search ............................. 560/312; 556/419

[56] References Cited

FOREIGN PATENT DOCUMENTS

0299914B1   4/1993   European Pat. Off. .

OTHER PUBLICATIONS

Buchmann et al., "Synthesis of a Chemically and Metabolically Stable", *Tetrahedron Letters*, Vol. 31, No. 24, pp. 3425–3428 (1990).

Cooper et al., "Synthesis of the Four Stereoisomers of Enprostil[1,2]", *Journal of Organic Chemistry*, vol. 58, pp. 4280–4286 (1993).

Mills et al., "Diastereospecific, Non–Racemic Synthesis of the C.20–C.34 Segment of the Novel Immunosuppressant FK–506", *Tetrahedron Letters*, vol. 29(3), pp. 281–284 (1988).

Schaaf et al., "Synthesis of 11α,9α–Epoxymethanothromboxane A$_2$: A Stable, Optically Active TxA$_2$ Agonist", *J. Am. Chem. Soc.*, vol. 103, pp. 6502–6505 (1981).

*Primary Examiner*—Robert Gerstl
*Attorney, Agent, or Firm*—Michael C. Mayo

[57] ABSTRACT

Novel N-alkyl-N-alkoxycarboxamides useful for prostaglandin synthesis are disclosed. Also disclosed are novel synthetic methods for preparing the novel intermediates of the present invention.

4 Claims, No Drawings

N-ALKYL-N-ALKOXYCARBOXAMIDES AND METHODS OF USE IN PROSTAGLANDIN SYNTHESIS

This application claims priority from co-pending U.S. Provisional Patent Application Ser. No. 60/068,114, filed Dec. 19, 1997.

The present invention is directed to novel intermediates useful in prostaglandin synthesis. More specifically, the invention is directed to N-alkyl-N-alkoxycarboxamides and methods for the synthesis of prostaglandins.

BACKGROUND OF THE INVENTION

Naturally occurring prostaglandins are biologically active in a myriad of ways including hormone action, muscular contraction/relaxation, platelet aggregation/inhibition, intraocular pressure reduction and other cellular transduction mechanisms. Prostaglandins are enzymatically produced in nature from arachidonic acid. The arachidonic acid cascade is initiated by the prostaglandin synthase catalyzed cyclization of arachidonic acid to prostaglandin $G_2$ and subsequent conversion to prostaglandin $H_2$. Other naturally occurring prostaglandins are derivatives of prostaglandin $H_2$. A number of different types of prostaglandins have been discovered including A, B, C, D, E, F and I-Series prostaglandins. These descriptions delineate substitution patterns of the various cyclopentane group central to all prostaglandins. Still other naturally occurring derivatives include thromboxane A2 and B2.

Due to their potent biological activity, prostaglandins have been studied for possible pharmaceutical benefit. However, due to potency of these molecules, as well as the ubiquitous presence of these agents and receptors and other biologically responsive tissue sites to their presence, numerous side effects have prevented the exploitation of the naturally occurring prostaglandins. It has also been difficult to pharmaceutically exploit the naturally occurring prostaglandins due to the relatively unstable nature of these molecules. As a result, researchers have been preparing and testing synthetic prostaglandin analogs, known as "prostanoids," for several decades.

In general, prostanoids can be described generically as consisting of (1) an alpha chain; (2) an omega chain; and (3) a cyclopentane group (or a heterocycle or other ring structure), as shown in formula (I).

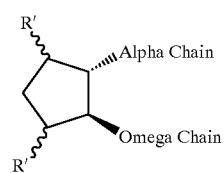

(I)

In general, the R' groups of the ring structure are independently hydroxy, oxy, halogen and hydrogen groups. The omega chain has generally consisted of linear carbon backbones of varying lengths. The omega chains have also been of varying degrees of saturation, containing optional heteroatoms and have terminated with a variety of alkyl and cycloalkyl groups. Alpha chains have consisted of numerous linear moieties and have involved various degrees of saturation. The alpha chains generally consist of a seven carbon chain and generally terminate with a carboxylic acid group or a variety of corresponding esters.

Another set of prostaglandins of particular interest are known as the "3-oxa-prostaglandins" or "3-oxa-prostanoids," which contain an oxygen atom at the three position, according to formula (II):

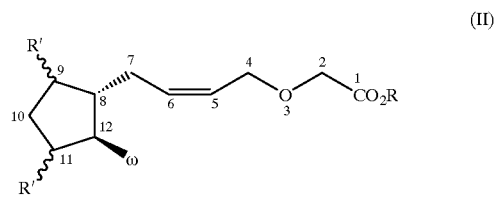

(II)

wherein, R' is oxy, hydroxy, halogen, protected hydroxy or hydrogen; and the omega chain is generally five to twelve carbons in length with various substitutions including substitutions of hetero-atoms within the chain.

The compounds of formula (II) are typically synthesized by methods outlined in Scheme A, below, similar to methods disclosed in Buchmann et al., *Tetrahedron Letters*, volume 31, page 3425 (1990) and European Patent No. 0299914.

Scheme A

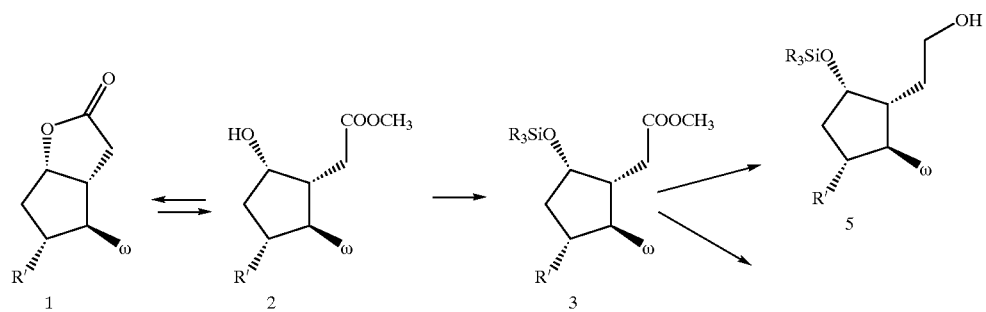

-continued

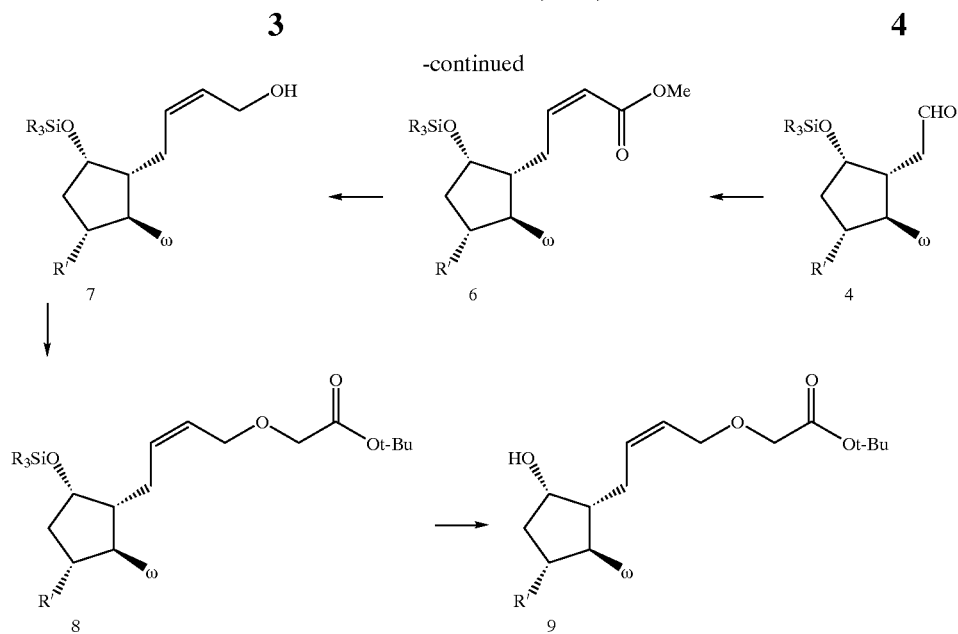

Generally, a lactone (1), wherein R' can be a hydroxy, halogen, protected hydroxy or hydrogen moiety and ω is an omega chain as generally known in the art, is converted to a hydroxy ester (2). The ester (2) is then silylated to give a protected hydroxy ester (3). Reduction of the protected hydroxy ester (3) yields a protected hydroxy aldehyde (4) and a side product alcohol (5). The protected hydroxy aldehyde (4) is then condensed with a trialkyl phosphonoacetate salt to give the unsaturated ester (6). Reduction of the ester (6) produces the allylic alcohol (7) which is then converted to the protected 3-oxa prostaglandin (8) by alkylation of the primary hydroxyl and the deprotected 3-oxa prostaglandin (9) by desilyation. The 3-oxa prostaglandin (9) can be further processed to yield a 9-keto or 9-halo analog and/or, to give an alpha chain terminating ester of choice.

The protected hydroxy aldehyde (4) is thus a key intermediate in the synthesis of 3-oxa prostanoids. The above synthetic route of Scheme A, however, is complicated by undesired side reactions which can result in poor yields, and the generation of substantial by-products. One problem is due to the reversible nature of the lactone ring opening reaction, i.e., (1) forming (2). The hydroxy ester (2) is unstable with respect to reclosure to lactone (1). In fact, in some cases the lactone (1) is preferred over the ester (2), causing poor yields of the protected hydroxy ester (3) and hence, poor yields of the protected aldehyde product (4).

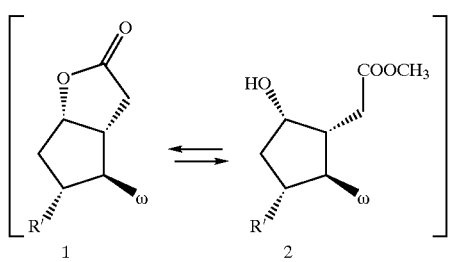

Another problem with the above synthetic method is the formation of the by-product (5), the monoprotected diol. The unwanted by-product (5), which can result from uncontrolled reduction of (3), will not convert to the desired product (4) without further processing. Thus, low yields of (4) result in poor yields of the desired product. See for example, Cooper et al., *Journal Of Organic Chemistry*, volume 58, page 4280 (1993).

A need has arisen, therefore, to develop superior synthetic methods which allow the preparation of the various prostanoids of interest in greater yields.

SUMMARY OF THE INVENTION

The present invention is directed to novel prostaglandin intermediates and novel methods employing those novel intermediates in the synthesis of prostaglandins. More specifically, the invention is directed to N-alkyl-N-alkoxycarboxamides and methods for the synthesis of prostaglandins. The N-alkyl-N-alkoxycarboxamides are prepared by the amidation of a lactone and protection of the resulting free hydroxy from the opening of the ring.

The use of the N-alkyl-N-alkoxycarboxamide intermediates obviates cyclization problems existing with traditional synthetic methods involving ring scission of a lactone. The avoidance of cyclization provides for greater yield of the protected aldehyde intermediate.

The use of the N-alkyl-N-alkoxycarboxamide intermediates also avoids alcohol by-product formation typical in 3-oxa prostaglandin synthesis. The avoidance of this by-product also provides for greater yield of the protected aldehyde intermediate.

Preferred methods of the present invention employ the novel intermediates of the present invention in the synthesis of 3-oxa prostaglandins.

DETAILED DESCRIPTION OF THE INVENTION

The novel intermediates of the present invention are those of formulas (IV) and (V):

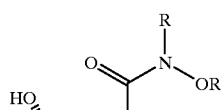

(IV)

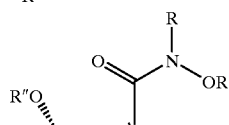

(V)

wherein,

R is $C_{1-4}$ alkyl;

R' is hydroxy, halogen, protected hydroxy or hydrogen;

R" is a protecting group, e.g., trialkyl($C_{1-4}$)silyl; and

ω is

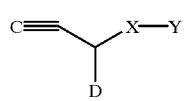

wherein:

--- is an optional bond;

D may be in the α or β configuration, and is fluorine or $OR^4$, wherein $R^4$ is H, alkyl, alkoxyalkyl, acyl, or $Si(R^6)_3$, wherein $R^6$ is independently $C_{1-4}$ alkyl or phenyl;

X is $(CH_2)_m$ or $(CH_2)_mO$, wherein m is 1 to 6; and

Y is a phenyl ring optionally substituted with alkyl, halo, trihalomethyl, alkoxy, acyl, acyloxy, amino, alkylamino, acylamino, or hydroxy; or X—Y is $(CH_2)_pY^1$; wherein p is 0 to 6; and $Y^1 = $ 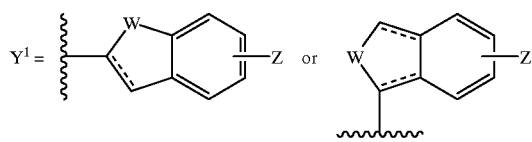

wherein:

W is $CH_2$, O, $S(O)_q$, $NR^5$, $CH_2CH_2$, CH=CH, $CH_2O$, $CH_2S(O)_q$, CH=N, or $CH_2NR^5$; wherein q is 0 to 2, and $R^5$ is H, alkyl, or acyl;

Z is H, alkyl, alkoxy, acyl, acyloxy, halo, trihalomethyl, amino, alkylamino, acylamino, or hydroxy; and --- is an optional bond; or X—Y is cyclohexyl.

Preferred intermediates of formulas (IV) and (V) are those having an ω chain consisting of:

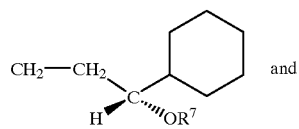

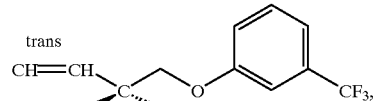

wherein $R^7$ is $SiPh_2$t-Bu or tetrahydropyranyl.

The novel intermediates of formulas (IV) and (V) can be synthesized following Scheme B, below:

Scheme B

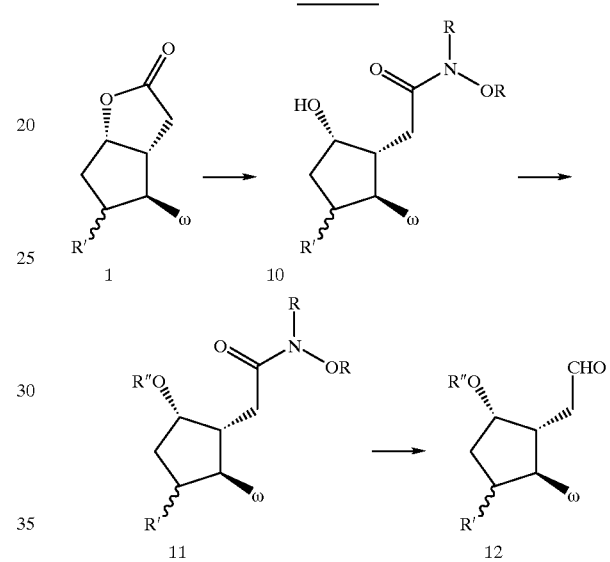

In Scheme B, the lactone (1), wherein R, R' (excluding oxy), R" and ω are defined as above, is first amidated to give the hydroxy (N-alkyl-N-alkoxycarboxamide) (10). The free hydroxy group of (10) is then protected with a protecting group R", to yield the protected hydroxy (N-alkyl-N-alkoxycarboxamide) (11). Various protecting groups can be employed using methods known to those skilled in the art. For example, the hydroxy (N-alkyl-N-alkoxycarboxamide) (10) can be protected with a trialkyl ($C_{1-4}$) silyl group.

The protected hydroxy(N-alkyl-N-alkoxycarboxamide) (11) can now be prepared for prostaglandin synthesis. For example, the carboxamide (11) (formula V) can now be reacted with a reducing agent, such as lithium aluminum hydride or DIBAL, to form the protected aldehyde (12):

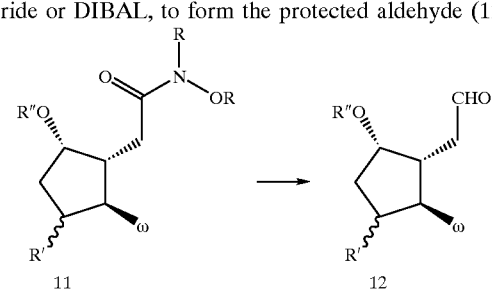

The product (12) can now be inserted in place of the protected aldehyde product (4) of known methods of 3-oxa prostaglandin synthesis. For example, the product (12) can be used to synthesize 3-oxa prostaglandins according to Scheme C, below:

Scheme C

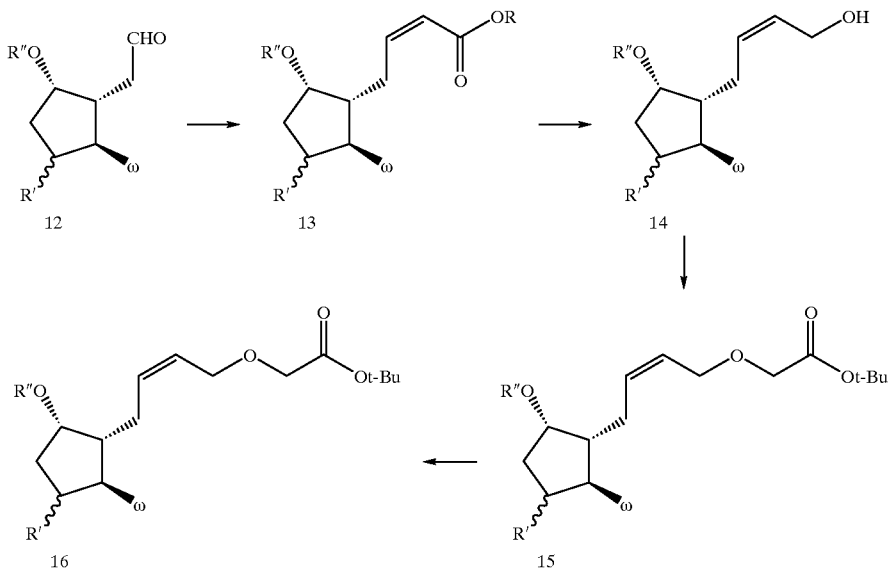

Generally, the 3-oxa prostaglandins of Scheme C can be prepared by reacting the protected aldehyde (12) (generated from the novel intermediates and methods of the present invention), wherein R, R' (excluding oxy), R" and ω are defined above, with a trialkyl phosphonoacetate salt to give the unsaturated ester (13). The unsaturated ester (13) is then reduced with a metal hydride reducing agent to form the allylic alcohol (14). The alcohol (14) is then converted to the protected 3-oxa prostaglandin (15) by alkylation of the primary hydroxyl group. The protected 3-oxa prostaglandin is then deprotected by methods known to those skilled in the art, e.g., Greene et al., *Protective Groups in Organic Synthesis*, $2^{nd}$ ed., Wiley: New York, 1991; to give the free hydroxyl 3-oxa prostaglandin (16). The free hydroxyl of (16) can be further processed by methods known in the art to give the corresponding 9-keto or 9-halo prostaglandin. Further processing can be employed to give an analog of (16) containing an alpha chain terminating ester of choice.

The methods of the present invention are also useful in preparing the 3-carba prostaglandins of formula (III):

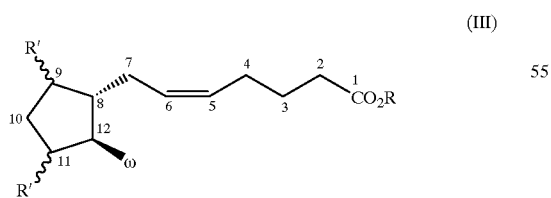

(III)

wherein, R, R' (and including oxy) and ω are defined as above. For example, the product (12) can be used to synthesize 3-carba prostaglandins according to Scheme D, below:

Scheme D

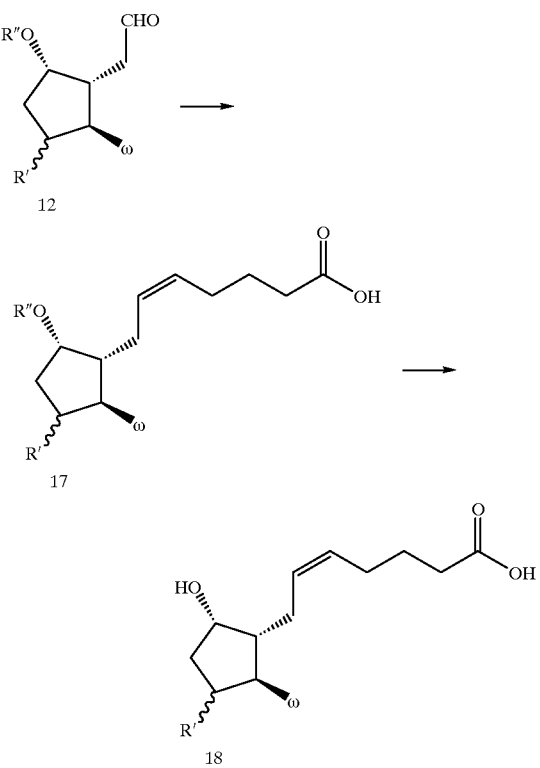

Generally, the 3-carba prostaglandins of Scheme D can be prepared by reacting the protected aldehyde (12) (generated from the novel intermediates and methods of the present invention) with a phosphorane to form the unsaturated acid (17). The acid (17) is then deprotected by methods known to those skilled in the art (see, e.g., Greene et al., *Protective Groups in Organic Synthesis*, $2^{nd}$ ed., Wiley: New York, 1991), to give the free hydroxyl 3-carba prostaglandin. The free hydroxyl compound (18) can be further processed by methods known in the art to give the corresponding 9-keto or 9-halo prostaglandin, and/or further processed to give an alpha chain terminating ester of choice.

The following examples further illustrate preferred syntheses of preferred novel intermediates of the present invention:

EXAMPLE 1
Step 1:

Trimethylaluminum (0.28 milliliters ("mL")) of a 2.0 molar ("M") toluene solution) was added to a stirred ice-cooled suspension of N,O-dimethylhydroxylamine hydrochloride (54 mg, 0.55 millimoles ("mmol")) in 0.5 mL of toluene under argon. The cooling bath was removed and the mixture was stirred for 20 minutes as methane was evolved. The mixture was cooled in ice, and a solution of (3aR, 4R, 5R, 6aS)-4-[(3R)-3-cyclohexyl-3-(t-butyldiphenylsilyloxy)propyl]-hexahydro-5-(t-butyldiphenylsilyloxy)-2H-cyclopenta[b]furan-2-one (0.14 g, 0.185 mmol) in 0.6 mL of toluene was added via syringe. The cooling bath was removed and the mixture was stirred for 1.5 hours, then cooled in ice. Methanol (0.3 mL) was added causing gas evolution and formation of a precipitate. Saturated aqueous potassium sodium tartrate was added, followed by a 3:1 solution of ether and ethyl acetate. The organic solution was separated, dried over anhydrous $MgSO_4$, filtered through Florisil and concentrated to give 0.12 g (79%) of (9S, 11R, 15R)-11,15-bis-(t-butyldiphenylsilyloxy)-15-cyclohexyl-2,3,4,5,6,16,17,18,19,20-decanor-9-hydroxyprostanoic (N-methoxy-N-methyl) amide as a foam.

$NMR(CDCl_3)$ δ 1.01 (s, 9H), 1.04 (s, 9H), 0.8–1.9 (m, 19H), 2.35 (m, 1H), 2.85 (dd, 1H), 3.20 (s, 3H), 3.2 (d, 1H, exchanges), 3.30 (m, 1H), 3.70 (s, 3H), 3.81 (br s, 1H), 4.12 (br q, 1H), 7.3 (m, 12H), 7.6 (m, 8H).

Step 2:

Triethylsilyl chloride (0.08 mL, 0.48 mmol) was added to a stirred solution of 4-dimethylaminopyridine (10 mg, 0.08 mmol), triethylamine (0.10 mL, 0.7 mmol), and (9S, 11R, 15R)-11,15-bis-(t-butyldiphenylsilyloxy)-15-cyclohexyl-2,3,4,5,6,16,17,18,19,20-decanor-9-hydroxyprostanoic (N-methoxy-N-methyl)amide (0.10 g, 0.12 mmol) in dichloromethane (1.0 mL) under argon. After stirring overnight, the mixture was diluted with ether-hexane (1:1) and extracted with saturated aqueous $KH_2PO_4$ (twice), water and brine, dried over anhydrous $MgSO_4$, filtered and concentrated to give 0.11 g (97%) of (9S, 11R, 15R)-11,15-bis-(t-butyldiphenylsilyloxy)-15-cyclohexyl-2,3,4,5,6,16,17,18,19,20-decanor-9-(triethylsilyloxy)prostanoic (N-methoxy-N-methyl)amide as an oil.

$NMR(CDCl_3)$ δ 0.5 (overlapping q, 6H), 0.9 (overlapping t, 9H), 1.0 (s, 18H), 0.8–1.9 (m, 19H), 2.2 (m, 1H), 2.75 (m, 1H), 3.15 (s, 3H), 3.32 (br s, 1H), 3.64 (s, 3H), 396 (br q, 11H), 7.3 (m, 12H), 7.6 (m, 8H).

Step 3:

Diisobutylaluminum hydride (0.11 mL of a 1.5 M toluene solution) was added to a stirred, cooled (−70° C.) solution of (9S, 11R, 15R)-11,15-bis-(t-butyldiphenylsilyloxy)-15-cyclohexyl-2,3,4,5,6,16,17,18,19,20-decanor-9-(triethylsilyloxy)prostanoic (N-methoxy-N-methyl)amide (0.10 g, 0.11 mmol) in 1.5 mL of dry tetrahydrofuran under argon. After 1 hour, methanol (0.5 mL) was added and the solution was allowed to warm to 0° C., then diluted with ether-hexane (1:1). Saturated aqueous $KH_2PO_4$ was added and the mixture was stirred vigorously for 1 hour. The organic solution was separated, dried over anhydrous $MgSO_4$, filtered and concentrated to give 0.09 g (95%) of (9S, 11R, 15R)-11,15-bis-(t-butyldiphenylsilyloxy)-15-cyclohexyl-2,3,4,5,6,16,17,18,19,20-decanor-9-(triethylsilyloxy) prostanal as an oil.

$NMR(CDCl_3)$ δ 0.5 (overlapping q, 6H), 0.9 (overlapping t, 9H), 1.01 (s, 18H), 0.8–1.9 (m, 19H), 2.1 (dd, 1H), 2.6 (m, 1H), 3.35 (br q, 1H), 3.62 (q, 1H), 3.87 (q, 1H), 7.3 (m, 12H), 7.6 (m, 8H), 9.63 (t, 1H).

EXAMPLE 2

This synthesis example is analogous to the Example 1 method, but prepared on a larger scale.

Step 1:

Trimethylaluminum (5.2 mL of a 2.0 M toluene solution) was added to a stirred ice-cooled suspension of N,O-dimethylhydroxylamine hydrochloride (1.03 g, 10.6 mmol) in 12 mL of toluene under argon. The cooling bath was removed and the mixture was stirred for 30 minutes as methane was evolved. A solution of (3aR, 4R, 5R, 6aS)-4-[(3R)-3-cyclohexyl-3-(t-butyldiphenylsilyloxy)propyl]-hexahydro-5-(t-butyldiphenylsilyloxy)-2H-cyclopenta[b] furan-2-one (4.05 g, 5.34 mmol) in 22 mL of toluene was added via syringe. The mixture was stirred for 1.5 hours, then cooled in ice. Methanol (2 mL) was added causing gas evolution and formation of a precipitate. Saturated aqueous potassium sodium tartrate and ethyl acetate were added, and the mixture was stirred vigorously and allowed to warm to room temperature. The organic solution was separated, dried over anhydrous $MgSO_4$, eluted through Florisil with ethyl acetate and concentrated. The crude product was purified by chromatography on silica, to give 3.97 g (91%) of (9S, 11R, 15R)-11,15-bis-(t-butyldiphenylsilyloxy)-15-cyclohexyl-2,3,4,5,6,16,17,18,19,20-decanor-9-hydroxyprostanoic (N-methoxy-N-methyl)amide as a viscous oil.

Step 2:

Triethylsilyl chloride (4.0 mL, 24 mmol) was added to a stirred solution of 4-dimethylaminopyridine (0.60 g, 5.0 mmol), triethylamine (4.2 mL, 30 mmol), and (9S, 11R, 15R)-11,15-bis-(t-butyldiphenylsilyloxy)-15-cyclohexyl-2,3,4,5,6,16,17,18,19,20-decanor-9-hydroxyprostanoic (N-methoxy-N-methyl)amide (3.95 g, 4.82 mmol) in dichloromethane (20 mL) under argon. After stirring for four hours, the mixture was cooled in ice, quenched with methanol (2 mL), allowed to warm to room temperature, then diluted with ether, extracted with saturated aqueous $KH_2PO_4$ (twice), water and brine, dried over anhydrous $MgSO_4$, filtered and concentrated to give 4.65 g (100%) of (9S, 11R, 15R)-11,15-bis-(t-butyldiphenylsilyloxy)-15-cyclohexyl-2,3,4,5,6,16,17,18,19,20-decanor-9-(triethylsilyloxy) prostanoic (N-methoxy-N-methyl)amide as an oil. This material was used in the following step without purification.

Step 3:

Diisobutylaluminum hydride (5.1 mL of a 1.0 M toluene solution) was added to a stirred, cooled (−70° C.) solution of (9S, 11R, 15R)-11,15-bis-(t-butyldiphenylsilyloxy)-15-cyclohexyl-2,3,4,5,6,16,17,18,19,20-decanor-9-(triethylsilyloxy)prostanoic (N-methoxy-N-methyl)amide (4.60 g, 4.93 mmol) in 40 mL of dry tetrahydrofuran under argon. After 1.3 hours, 1.5 mL of 1.0 M diisobutylaluminum hydride in toluene was added. After 40 minutes, methanol (0.5 mL) was added and the solution was allowed to warm to 0° C., then diluted with ether-hexane (1:1). Saturated aqueous $KH_2PO_4$ was added and the mixture was stirred vigorously for 20 minutes. Saturated aqueous potassium sodium tartrate was added, and stirring was continued for 10 minutes. The organic solution was separated, dried over anhydrous $MgSO_4$, filtered and concentrated. The crude product was purified by chromatography on silica to give 3.92 g (91%) of (9S, 11R, 15R)-11,15-bis-(t- butyldiphenylsilyloxy)-15-cyclohexyl-2,3,4,5,6,16,17,18, 19,20-decanor-9-(triethylsilyloxy) prostanal as an oil.

The (9S, 11R, 15R)-11,15-bis-(t-butyldiphenylsilyloxy)-15-cyclohexyl-2,3,4,5,6,16,17,18,19,20-decanor-9-(triethylsilyloxy)prostanal product of the above Examples 1 and 2 may now be used in various prostaglandin syntheses known to those skilled in the art. For example, the product may be inserted in Scheme C or D, for the preparation of 3-oxa or 3-carba prostaglandins, respectively. Other examples of prostaglandin synthesis for which the product would be a useful intermediate include methods disclosed in commonly assigned U.S. Pat. No. 5,721,273 (Sallee et al.).

EXAMPLE 3

Step 1:

Using the method described in Example 2, step 1, with adjustments for scale, 1.70 g (3.15 mmol) of (3aR, 4R, 5R, 6aS)-5-(tetrahydropyran-2-yl)oxy-4-(4-(3-trifluoromethylphenoxy)-3R-(tetrahydropyran-2-yl)oxy-1E-butenyl)-hexahydro-2H-cyclopenta[b]furan-2-one afforded 1.47 g (78%) of (9S, 11R, 15R)-11,15-bis-(tetrahydropyran-2-yl)oxy-16-(3-trifluoromethylphenoxy)-2,3,4,5,6,17,18,19, 20-nonanor-9-hydroxyprostanoic (N-methoxy-N-methyl) amide as a viscous oil.

NMR(CDCl$_3$) δ 1.3–2.1 (m, 14H), 2.2–2.8 (m, 4H), 2.95 (d, 1H, exchanges), 3.17 (s, 3H), 3.5 (m, 2H), 3.65 (s, 3H), 3.7–4.2 (m, 5H), 4.26 (br s, 1H), 4.53 (br d, 1H), 4.6–5.0 (m, 2H), 5.4–5.8 (m, 2H), 7.0–7.2 (m, 3H), 7.38 (t, 1H).

Step 2:

Using the method described in Example 2, step 2, with adjustments for scale, 1.45 g (2.41 mmol) of (9S, 11R, 15R)-11,15-bis-(tetrahydropyran-2-yl)oxy-16-(3-trifluoromethylphenoxy)-2,3,4,5,6,17,18,19,20-nonanor-9-hydroxyprostanoic (N-methoxy-N-methyl)amide afforded 1.68 g (97%) of (9S, 11R, 15R)-11,15-bis-(tetrahydropyran-2-yl)oxy-16-(3-trifluoromethylphenoxy)-2,3,4,5,6,17,18,19, 20-nonanor-9-(triethylsilyloxy) prostanoic (N-methoxy-N-methyl) amide as a viscous oil.

NMR(CDCl$_3$) δ 0.57 (overlapping q, 6H), 0.93 (t, 9H), 1.3–2.0 (m, 14H), 2.0–2.9 (m, 4H), 3.10 (s, 3H), 3.5 (m, 2H), 3.56 (s, 11H), 3.7–4.2 (m, 5H), 4.3 (br s, 1H), 4.5 (br s, 1H), 4.6–5.0 (m, 2H), 5.4–5.8 (m, 2H), 7.0–7.2 (m, 3H), 7.37 (t, 3H).

Step 3:

Using the method described in Example 2, Step 3, with adjustments for scale, 1.65 g (2.31 mmol) of (9S, 11R)-11, 15-bis-(tetrahydrophyran-2-yl)oxy-16-(3-trifluoromethylphenoxy)-2,3,4,5,6,17,18,19,20-nonanor-9-(triethylsilyloxy)prostanoic (N-methoxy-N-methyl)amide afforded 1.19 g (79%) of (9S, 11R, 15R)-11,15-bis (tetrahydropyran-2-yl)oxy-16-(3-trifluoromethylphenoxy)-2,3,4,5,6,17,18,19,20-nonanor-9-(triethylsilyloxy)prostanal as a viscous oil.

NMR(CDCl$_3$) δ 0.56 (overlapping q, 6H), 0.93 (t, 9H), 1.3–1.9 (m, 13H), 2.1 (m, 1H), 2.2–2.9 (m, 4H), 3.6 (m, 2H), 3.7–4.2 (m, 5H), 4.25 (br d, 1H), 4.50 (br s, 1H), 4.55–5.0 (m, 2H), 5.4–5.8 (m, 2H), 7.0–7.2 (m, 3H), 7.38 (t, 1H), 9.77 (s, 1H).

The (9S, 11R, 15R)-11,15-bis(tetrahydropyran-2-yl)oxy-16-(3-trifluoromethylphenoxy)-2,3,4,5,6,17,18,19,20-nonanor-9-(triethylsilyloxy)prostanal product of the above Examples 1 and 2 may now be used in various prostaglandin syntheses known to those skilled in the art. For example, the product may be inserted in Scheme C or D, for the preparation of 3-oxa or 3-carba prostaglandins, respectively. Other examples of prostaglandin synthesis for which the product would be a useful intermediate include methods disclosed in commonly assigned U.S. Pat. No. 5,721,273 (Sallee et al.).

What is claimed is:

1. A compound of either formula (IV) or (V):

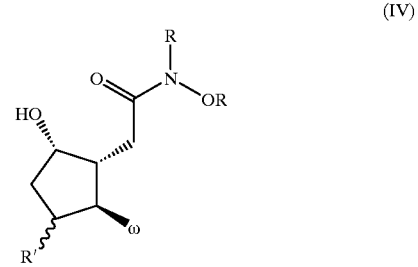
(IV)

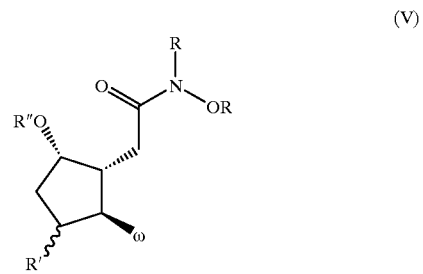
(V)

wherein,

R is $C_{1-4}$ alkyl;

R' is hydroxy, halogen, protected hydroxy or hydrogen;

R" is a protecting group; and

ω is

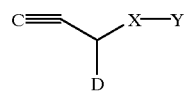

wherein:

≡ is a single, double or triple bond;

D may be in the α or β configuration, and is fluorine or OR$^4$, wherein R$^4$ is H, alkyl, alkoxyalkyl, acyl, or Si(R$^6$)$_3$, wherein R$^6$ is independently $C_{1-4}$ alkyl or phenyl;

X is (CH$_2$)$_m$ or (CH$_2$)$_m$O, wherein m is 1 to 6; and

Y is a phenyl ring optionally substituted with alkyl, halo, trihalomethyl, alkoxy, acyl, acyloxy, amino, alkylamino, acylamino, or hydroxy; or X—Y is (CH$_2$)$_p$Y$^1$; wherein p is 0 to 6; and

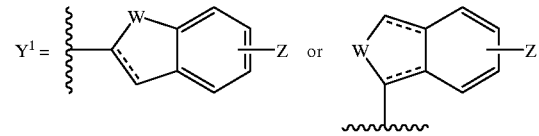

wherein:

W is CH$_2$, O, S(O)$_q$, NR$^5$, CH$_2$CH$_2$, CH=CH, CH$_2$O, CH$_2$S(O)$_q$, CH=N, or CH$_2$NR$^5$; wherein q is 0 to 2, and R$^5$ is H, alkyl, or acyl;

Z is H, alkyl, alkoxy, acyl, acyloxy, halo, trihalomethyl, amino, alkylamino, acylamino, or hydroxy; and --- is an optional bond; or X—Y is cyclohexyl.

2. A method of synthesizing a compound of formula (IV) or (V):

(IV)

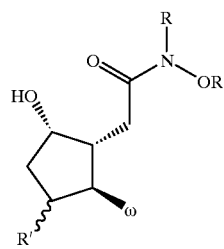

(V)

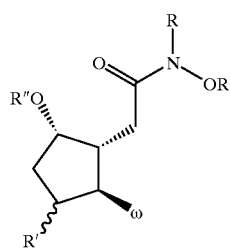

wherein,

R is $C_{1-4}$ alkyl;

R' is hydroxy, halogen, protected hydroxy or hydrogen;

R" is a protecting group; and

ω is

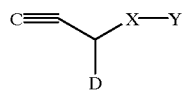

wherein:

≡ is a single, double or triple bond;

D may be in the α or β configuration, and is fluorine or $OR^4$, wherein $R^4$ is H, alky, alkoxyalkyl, acyl, or $Si(R^6)_3$, wherein $R^6$ is independently $C_{1-4}$ alkyl or phenyl;

X is $(CH_2)_m$ or $(CH_2)_mO$, wherein m is 1 to 6; and

Y is a phenyl ring optionally substituted with alkyl, halo, trihalomethyl, alkoxy, acyl, acyloxy, amino, alkylamino, acylamino, or hydroxy; or X—Y is $(CH_2)_pY^1$; wherein p is 0 to 6; and

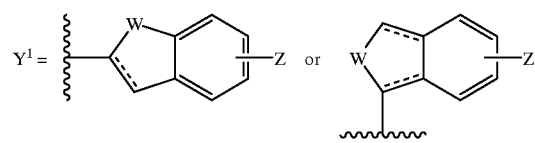

wherein:

W is $CH_2$, O, $S(O)_q$, $NR^5$, $CH_2CH_2$, CH=CH, $CH_2O$, $CH_2S(O)_q$, CH=N, or $CH_2NR^5$; wherein q is 0 to 2, and $R^5$ is H, alkyl, or acyl;

Z is H, alkyl, alkoxy, acyl, acyloxy, halo, trihalomethyl, amino, alkylamino, acylamino, or hydroxy; and --- is an optional bond; or X—Y is cyclohexyl;

comprising the steps of:

A) amidating a compound of formula (VI)

(VI)

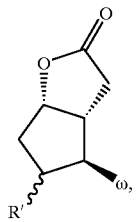

to give a hydroxy (N-alkyl-N-alkoxycarboxamide) of formula (IV); and

B) protecting the hydroxy (N-alkyl-N-alkoxycarboxamide) with a protecting group to yield a protected hydroxy (N-alkyl-N-alkoxycarboxamide) of formula (V).

3. A method of synthesizing a 3-oxa prostaglandin or prostanoid comprising the steps of:

A) reacting a compound of formula (V)

(V)

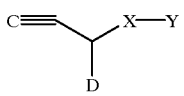

wherein,

R is $C_{1-4}$ alkyl;

R' is hydroxy, halogen, protected hydroxy or hydrogen;

R" is a protecting group; and

ω is

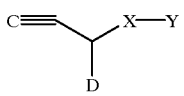

wherein:

≡ is a single, double or triple bond;

D may be in the α or β configuration, and is fluorine or $OR^4$, wherein $R^4$ is H, alkyl, alkoxyalkyl, acyl, or $Si(R^6)_3$, wherein $R^6$ is independently $C_{1-4}$ alkyl or phenyl;

X is $(CH_2)_m$ or $(CH_2)_mO$, wherein m is 1 to 6; and

Y is a phenyl ring optionally substituted with alkyl, halo, trihalomethyl, alkoxy, acyl, acyloxy, amino, alkylamino, acylamino, or hydroxy; or X—Y is $(CH_2)_pY^1$; wherein p is 0 to 6; and

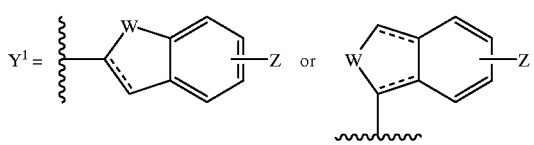

wherein:

W is $CH_2$, O, $S(O)_q$, $NR^5$, $CH_2CH_2$, CH=CH, $CH_2O$, $CH_2S(O)_q$, CH=N, or $CH_2NR^5$; wherein q is 0 to 2, and $R^5$ is H, alkyl, or acyl;

Z is H, alkyl, alkoxy, acyl, acyloxy, halo, trihalomethyl, amino, alkylamino, acylamino, or hydroxy; and --- is an optional bond; or X—Y is cyclohexyl;

with a reducing agent to form a corresponding protected aldehyde of formula;

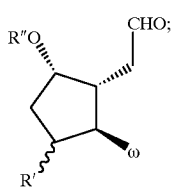

(VII)

B) reacting the protected aldehyde of formula (VII) with a trialkyl phosphonoacetate salt to give a corresponding unsaturated ester;

C) reducing the unsaturated ester with a reducing agent to form a corresponding allylic alcohol;

D) converting the allylic alcohol to a protected 3-oxa prostaglandin by alkylation of the alcohol; and E) deprotecting the protected 3-oxa prostaglandin to give a free hydroxyl 3-oxa prostagiandin.

4. A method of synthesizing a 3-carba prostaglandin or prostanoid comprising the steps of:

A) reacting a compound of formula (V)

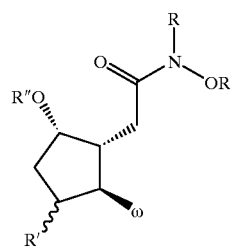

(V)

wherein,

R is $C_{1-4}$ alkyl;

R' is hydroxy, halogen, protected hydroxy or hydrogen;

R" is a protecting group; and

ω is

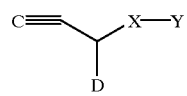

wherein:

≡ is a single, double or triple bond;

D may be in the α or β configuration, and is fluorine or $OR^4$, wherein $R^4$ is H, alkyl, alkoxyalkyl, acyl, or $Si(R^6)_3$, wherein $R^6$ is independently $C_{1-4}$ alkyl or phenyl;

X is $(CH_2)_m$ or $(CH_2)_mO$, wherein m is 1 to 6; and

Y is a phenyl ring optionally substituted with alkyl, halo, trihalomethyl, alkoxy, acyl, acyloxy, amino, alkylamino, acylamino, or hydroxy; or X—Y is $(CH_2)_pY^1$; wherein p is 0 to 6; and

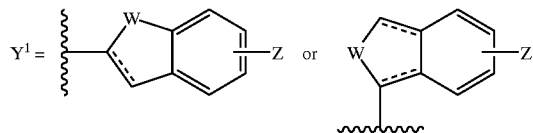

wherein:

W is $CH_2$, O, $S(O)_q$, $NR^5$, $CH_2CH_2$, CH=CH, $CH_2O$, $CH_2S(O)_q$, CH=N, or $CH_2NR^5$; wherein q is 0 to 2, and $R^5$ is H, alkyl, or acyl;

Z is H, alkyl, alkoxy, acyl, acyloxy, halo, trihalomethyl, amino, alkylamino, acylamino, or hydroxy; and --- is an optional bond; or X—Y is cyclohexyl;

with a reducing agent to form a corresponding protected aldehyde of formula

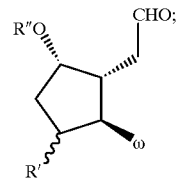

(VII)

B) reacting the protected aldehyde of formula (VII) with a phosphorane to form a corresponding unsaturated acid; and C) deprotecting the acid to give a corresponding free hydroxyl 3-carba prostaglandin.

* * * * *